US009495569B2

United States Patent
Theurer et al.

(10) Patent No.: US 9,495,569 B2
(45) Date of Patent: Nov. 15, 2016

(54) SYSTEM AND METHOD TO DETECT AN EVENT ASSOCIATED WITH A PERSON RELATIVE TO A BED

(71) Applicant: General Electric Company, Schenectady, NY (US)

(72) Inventors: Charles Theurer, Alplaus, NY (US); Judith Guzzo, Niskayuna, NY (US); Douglas Forman, Niskayuna, NY (US); Brandon Good, Schenectady, NY (US); Todd Scarola, Glen Allen, VA (US); Shaopeng Liu, Schenectady, NY (US); Robert Wallace, Glen Allen, VA (US); David Smith, Delmar, NY (US)

(73) Assignee: General Electric Company, Schenectady, NY (US)

( * ) Notice: Subject to any disclaimer, the term of this patent is extended or adjusted under 35 U.S.C. 154(b) by 418 days.

(21) Appl. No.: 14/135,870

(22) Filed: Dec. 20, 2013

(65) Prior Publication Data
US 2015/0178529 A1   Jun. 25, 2015

(51) Int. Cl.
  *G06K 7/10* (2006.01)
  *G06Q 50/22* (2012.01)
  *G06F 19/00* (2011.01)

(52) U.S. Cl.
  CPC ......... *G06K 7/10366* (2013.01); *A61B 90/90* (2016.02); *A61B 90/98* (2016.02); *G06F 19/327* (2013.01); *G06K 7/10316* (2013.01); *G06Q 50/22* (2013.01); *G06F 19/323* (2013.01)

(58) Field of Classification Search
  CPC .............. G06K 7/10366; G06K 7/10316; G06F 19/327; G06F 19/323; G06Q 50/22
  USPC ........................................ 340/10.1
  See application file for complete search history.

(56) References Cited

U.S. PATENT DOCUMENTS

| | | | |
|---|---|---|---|
| 4,320,766 A | 3/1982 | Alihanka et al. |
| 5,699,038 A | 12/1997 | Ulrich et al. |
| 5,983,076 A | 11/1999 | Takasan et al. |
| 6,897,780 B2 | 5/2005 | Ulrich et al. |
| 6,954,148 B2 | 10/2005 | Pulkkinen et al. |
| 7,113,087 B1 | 9/2006 | Casebolt et al. |
| 7,151,435 B2 | 12/2006 | Brackett et al. |

(Continued)

FOREIGN PATENT DOCUMENTS

WO    2013137892 A1    9/2013

OTHER PUBLICATIONS

GB Search Report and Examination Report from corresponding GB Application No. 1421925.7 dated May 26, 2015.

*Primary Examiner* — Edwin Holloway, III (57) ABSTRACT

A system and method to detect an event associated with a first object relative to a second object and a support is provided. The system can include an antenna at a support to receive the first object, a tag reader in communication with the antenna and a tag located on the second object. In response to detecting a change in impedance of the antenna associated with the presence of the first object, the tag reader communicates a presence signal. In response to detecting the tag within a threshold proximity of the tag reader, the tag reader generates a tag signal. A remoter server is operable to detect an association of the first and second objects based on a comparison a time associated with each of the tag signal and the presence signal, and in response then creates an output indicative of a detected event based on the association for illustration.

14 Claims, 4 Drawing Sheets

(56) References Cited

U.S. PATENT DOCUMENTS

| | | |
|---|---|---|
| 7,242,306 B2 | 7/2007 | Wildman et al. |
| 7,242,308 B2 | 7/2007 | Ulrich et al. |
| 7,458,118 B2 | 12/2008 | Bak |
| 7,466,232 B2 | 12/2008 | Neuwirth |
| 7,480,629 B2 | 1/2009 | Dashefsky et al. |
| 7,538,659 B2 | 5/2009 | Ulrich et al. |
| 7,633,392 B2 | 12/2009 | Neuwirth |
| 7,714,728 B2 | 5/2010 | Koblasz |
| 7,716,066 B2 | 5/2010 | Rosow et al. |
| 7,720,695 B2 | 5/2010 | Rosow et al. |
| 7,756,723 B2 | 7/2010 | Rosow et al. |
| 7,774,215 B2 | 8/2010 | Rosow et al. |
| 7,813,941 B2 | 10/2010 | Auker et al. |
| 7,852,208 B2 | 12/2010 | Collins et al. |
| 7,855,656 B2 | 12/2010 | Maschke et al. |
| 7,890,347 B2 | 2/2011 | Rosow et al. |
| 7,953,610 B2 | 5/2011 | Rosow et al. |
| 8,125,339 B2 | 2/2012 | Neuwirth |
| 8,150,709 B2 | 4/2012 | Miller et al. |
| 8,219,416 B2 | 7/2012 | Auker et al. |
| 8,258,965 B2 | 9/2012 | Reeder et al. |
| 8,280,748 B2 | 10/2012 | Allen et al. |
| 8,284,047 B2 | 10/2012 | Collins et al. |
| 8,323,189 B2 | 12/2012 | Tran et al. |
| 2002/0151990 A1 | 10/2002 | Ulrich et al. |
| 2005/0165325 A1 | 7/2005 | Hornig |
| 2006/0111939 A1 | 5/2006 | Bixler et al. |
| 2007/0129983 A1 | 6/2007 | Scherpbier et al. |
| 2007/0182553 A1* | 8/2007 | Kamizono ........ B60R 21/01534 340/561 |
| 2008/0033752 A1* | 2/2008 | Rodgers ................ G06F 19/327 705/2 |
| 2008/0065430 A1 | 3/2008 | Rosow et al. |
| 2008/0065431 A1 | 3/2008 | Rosow et al. |
| 2008/0065432 A1 | 3/2008 | Rosow et al. |
| 2008/0120784 A1 | 5/2008 | Warner et al. |
| 2008/0122616 A1* | 5/2008 | Warner ................ A61B 5/0002 340/541 |
| 2008/0126122 A1 | 5/2008 | Warner et al. |
| 2008/0126132 A1 | 5/2008 | Warner et al. |
| 2008/0147442 A1 | 6/2008 | Warner et al. |
| 2009/0096615 A1 | 4/2009 | Reeder et al. |
| 2009/0119127 A2 | 5/2009 | Rosow et al. |
| 2010/0073168 A1 | 3/2010 | Tallent et al. |
| 2010/0259390 A1* | 10/2010 | Borcherding ........ G06K 7/0008 340/572.1 |
| 2010/0272229 A1 | 10/2010 | Biber et al. |
| 2010/0321165 A1 | 12/2010 | Lee |
| 2011/0054297 A1 | 3/2011 | Bulitta et al. |
| 2012/0316892 A1 | 12/2012 | Huster et al. |
| 2012/0319836 A1 | 12/2012 | Reeder et al. |
| 2013/0007963 A1 | 1/2013 | Tallent et al. |
| 2013/0015866 A1* | 1/2013 | Wendt ............... B60R 21/01532 324/679 |
| 2014/0125355 A1* | 5/2014 | Grant .................... B64D 11/06 324/629 |
| 2015/0179053 A1* | 6/2015 | Good ................ A61B 5/6892 340/539.15 |

\* cited by examiner

SYSTEM AND METHOD TO DETECT AN EVENT ASSOCIATED WITH A PERSON RELATIVE TO A BED

TECHNICAL FIELD

The subject herein generally relates to a system and method to detect an event associated with an object relative to a support, and more specifically, to detect an event associated with a person on a bed based on a change in impedance of an antenna loop at the bed.

BACKGROUND

In a complex, sometime chaotic environment, there is a need for automatic detection and identification of events taking place to provide a view into utilization of assets as well as efficiency and quality. An example is a healthcare facility that delivers healthcare to patients that walk-in or delivered in emergency situations. Known methods to track and identify events have been manually implemented. Other known methods of tracking are based on active wireless tracking technology (e.g., operating at high frequency such as 915 MHz) that is accompanied with a high installation and maintenance cost. The above-mentioned problem can be addressed by the subject matter described herein in the following description.

BRIEF SUMMARY

The system and method of the subject matter described herein is directed to provide a system or method that can detect the event based on association of a presence of an object 110 at a location or support 120 relative to one or more other objects (e.g., caregiver personnel, equipment, etc.). In particular, this system and method can be used to detect different events associated with a protocol to deliver healthcare to a person located on or in proximity of a bed.

According to one embodiment, a system and method to detect an event associated with a first object relative to a second object and a support is provided. The system can include an antenna provided on a support to receive the first object, a tag reader in communication with the antenna and a tag located on the second object, and a remote server in communication with the tag reader. In response to detecting a change in impedance of the antenna associated with the presence of the first object, the tag reader communicates a presence signal to the remote server, and in response to detecting the tag within threshold proximity of the tag reader, the tag reader generates a tag signal for communication to a remote server. The remoter server is operable to detect an association of the first and second objects based on a comparison a time associated with each of the tag signal and the presence signal and in response then create an output indicative of the association for illustration indicative of occurrence of the event.

According to another embodiment, a method to detect an event associated with a first object relative to a second object and a support is provided. The method can include the steps of: providing an antenna to receive the first object relative to the support; detecting a change in impedance of the antenna associated with the presence of the first object via a tag reader; communicating a presence signal to the remote server in response to detecting the change in impedance; detecting the tag within a threshold proximity of the tag reader; generating a tag signal for communication to a remote server in response to detecting the tag within threshold proximity of the tag reader; detecting an association of the first and second objects at a remote server based on a comparison a time associated with each of the tag signal and the presence signal; and creating an output by the remote server indicative of the association for illustration indicative of the event.

Various other features, objects, and advantages of the invention will be made apparent to those skilled in the art from the accompanying drawings and detailed description thereof.

DETAILED DESCRIPTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
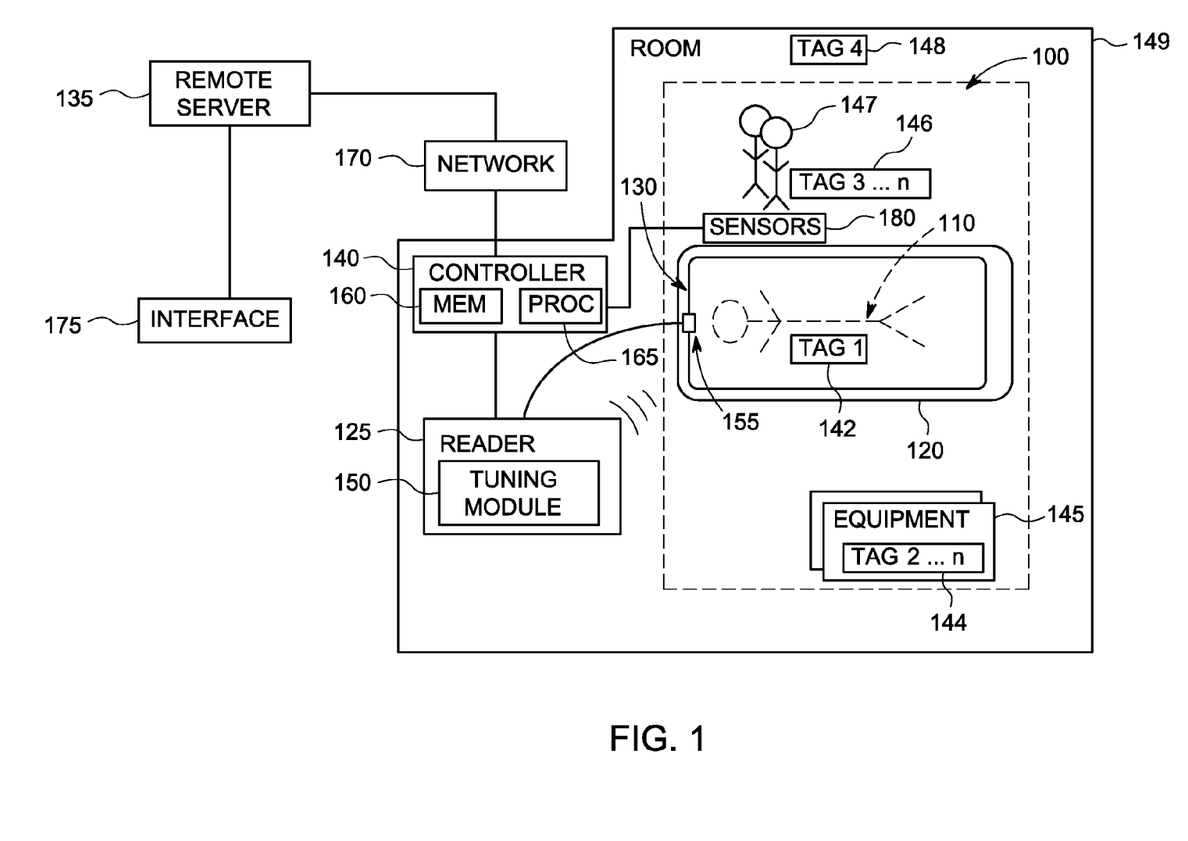
FIG. 1 is a schematic diagram of an embodiment of a system in accordance with the subject matter described herein.

FIG. 1 illustrates a schematic diagram of one embodiment of a system 100 to detect an event associated with a presence of an object 110 relative to a support 120. The following description is of one example of utilization of the system 100 directed to bed management at a healthcare facility (e.g., clinic, hospital), where the object 110 can be a person and the support 120 can be a bed or mattress or the like, as shown in FIG. 1. However, the utilization or application of the system 100 can vary. An embodiment of the system 100 can generally include a tag reader 125, an antenna circuit 130 at the support 120, and a remote server, computer or workstation or the like (herein "remote server 135"), and a controller 140.

The tag reader 125 can be generally operable to detect at least one tag 142 associated with the object 110, a tag 144 associated with an identifier of an equipment or device 145, a tag 146 associated with an identifier of a caregiver personnel 147, and a tag 148 associated with an identifier of the room 149 in proximity of the tag reader 125 using RFID technology. The tag reader 125 in operation with the tags 142, 144, 146, 148 can be passive such that do not transmit unless the tags 142, 144, 146, 148 receive an RFID signal transmitted within proximity of the tag reader 125.

The tag reader 125 can also be programmed to automatically detect a threshold deviation in impedance of the antenna circuit 130 from a norm or baseline impedance in response to the presence of the object 110. The measure of the change in impedance can be based on a measure of a first impedance of the antenna circuit 130 without the object 110 present and a second impedance of the antenna with the object 110 present. According to one embodiment, the tag reader 125 can be programmed or operable to measure change in the impedance or attenuation based on measure of a first resonant frequency of the test signal from the tag reader 125 that passes through the antenna circuit 130 without the object 110 present, for comparison with the measure of a second resonant frequency of the test signal that passes through the antenna circuit 130 with the object 110 present.

In response to detecting the deviation in impedance of the antenna circuit 130, the tag reader 125 can be programmed or operable to automatically adjust or change (e.g., add or subtract) impedance such that the measured impedance of the antenna circuit 130 in response to the test signal returns to within a threshold of the baseline impedance or range. To automatically change the impedance as described above so as to attain or return to a desired resonant frequency of the test signal that passes through the antenna circuit 130, the tag reader 125 can include a tuning module 150 operable to automatically add or subtract resistance, capacitance, inductance or combination thereof in series or parallel to the antenna circuit 130.

The tag reader 125 can also be operable to generate a presence signal indicative of a detected or measured threshold change or deviation in the impedance of the antenna circuit 130 to the test signal with the presence of the object 110. In the example shown in FIG. 1, the tag reader 125 can be operable to communicate the presence signal to the controller 140 in response to detecting the change in impedance caused by the presence of the object 110 (e.g., person) resting on the bed support 120. The measure or detection of the change in impedance of the antenna circuit 130 can be based on a change in pass-through parameters (e.g., resonant frequency) of the test signal through the antenna circuit 130, or based on the need to add or subtract impedance from the antenna circuit 130 to maintain the pass-through parameters (e.g., resonant frequency) of the test signal. In a like manner, the tag reader 125 can communicate the presence signal to the controller 140 in response to detecting or measuring the change in impedance of the antenna circuit 130 with the loss in presence (e.g., leaving the bed support 120) of the person.

The presence signal can generally include information or data indicative of an identification of the tag reader 125 or the antenna circuit 130. In another example, the tag reader 125 can be operable to detect an identification of tag 128 associated with the object 110, and thereby transmit the identification of the tag 152 or object 110 associated therewith independent of the presence signal to the controller 140.

An embodiment of the antenna circuit 130 can be of various composition of electrical conductivity (e.g., copper wire, silver wire, etc.) operable to transmit the test signal received from the tag reader 125. The shape of the antenna circuit 130 (e.g., circular, oval, rectangular, etc.) can vary. The antenna circuit 130 can be mounted at, attached to, or embedded within the structure of the support 120. According to the example shown in FIG. 1, the antenna circuit 130 extends near a general circumference of and embedded within the support 120, but is located to be a predefined space apart from an object 110 in the presence of the support 120. Yet, the antenna circuit 130 can be located around the circumference of the support 120, or beneath the support 120 and is not limiting of the subject matter described herein.

One embodiment of the antenna circuit 130 can be pre-tuned or configured to a predefined impedance (e.g. range or value of attenuation of a test signal measured as a resonant frequency) based on composition, structural dimensions, shape, etc. Another embodiment of the antenna circuit 130 can include a tuning circuit 155 operable to controllably adjust the impedance of the antenna circuit 130 within a predefined impedance when the object 110 is not on the support 120. An example of the resonant frequency can be 125 kHz or predefined threshold range (e.g., within frequency range of 120 kHz to 140 kHz) thereof, considered in the low frequency (LF) range. One example of the tuning circuit 155 can include slots to removeably install electric circuit components (e.g., capacitors, resistors, inductors, etc.) to add or subtract impedance in series or parallel so as to tune the antenna circuit 130 to a desired or predefined impedance (e.g., based on resonant frequency of test signal passing through).

The controller 140 can include memory 160 having programming instructions representative of steps for execution by a processor 165 in operating with the tag reader in detecting the presence of the object 110 relative to the support 120, as well as detecting proximity of tags 142, 144, 146, 148 associated with one or more objects 110 in the proximity of the tag reader 125. The memory 160 can be generally configured to store the program instructions for execution by the processor 165 to perform the steps in operation of the system 100, although some or all of the programmed instructions can be stored and/or executed elsewhere. A variety of different types of memory 160, such as a random access memory (RAM) or a read only memory (ROM) in the system 100 or a floppy disk, hard disk, CD ROM, DVD ROM, or other computer readable medium which is read from and/or written to by a magnetic, optical, or other reading and/or writing device that is coupled to the processor 165, can be used. The tag reader 125 can be located integrally as part of the controller 140 or independent/remote thereof and not be limiting on the subject matter described herein. An example of the processor 165 can be a central processing unit (CPU), but the type of processor 165 can vary.

The remote server 135 can be generally configured to communicate with the controller 140 over a wired or wireless network 170 (e.g., WI-FI, Internet, intranet, LAN, WAN, cloud, etc.) or combination thereof. According to one example, the remote server 135 can be programmed to calculate a correlation of the tag reader 125 to an identification of the room or defined space 149 where the tag reader 125 is located. In another example, the presence signal can include an identification of the tag 142 associated with the object 110 and detected by the tag reader 125.

The controller 140 or the remote server 135 can further include connection (wired or wireless) in communication with an interface 175. The interface 175 can include mechanisms receive input or to illustrate output to an operator of the system 100. Examples of the interface 175 can include a keyboard, touchscreen, a monitor, mouse, microphones, etc. know in the art to receive input from the operator. The interface 175 can also include a graphic illustration monitor, LEDs, speakers, etc. known in the art to provide output to the operator.

The system 100 can further include one or more types of sensors 180 in communication with the controller 140. One example of the sensors 180 can be of the pressure sensing type located at the support 120 to detect the pressure or track movement of the object 110 relative to the support 120. Yet, the number and type of the sensors 180 can vary. The controller 140 can generally be configured to communicate signals or data received from the sensors 180 to the remote server 135 for analysis with other received data associated with the presence signal, tag signals, etc. to calculate an occurrence of an event associated with delivery of healthcare to the object 110 (e.g., patient).

Having provided an embodiment of one construction of the system 100 in accordance with above-description, the following is a description of an embodiment of a method 200 (See FIGS. 2 and 3) to operate the system 100 in accordance with the subject matter described herein 100 to detect a presence of an object 110 (e.g. patient) relative to a support 120 (e.g., bed). It should also be understood that the sequence of the acts or steps of the method 200 as discussed in the foregoing description can vary. Also, it should be understood that the method 200 may not require each act or step in the foregoing description, or may include additional acts or steps not disclosed herein. It should also be understood that one or more of the steps of the method 200 can be represented by one or more computer program modules of computer-readable program instructions stored in the memory 160 for execution by the processor 165.

Figure 2:
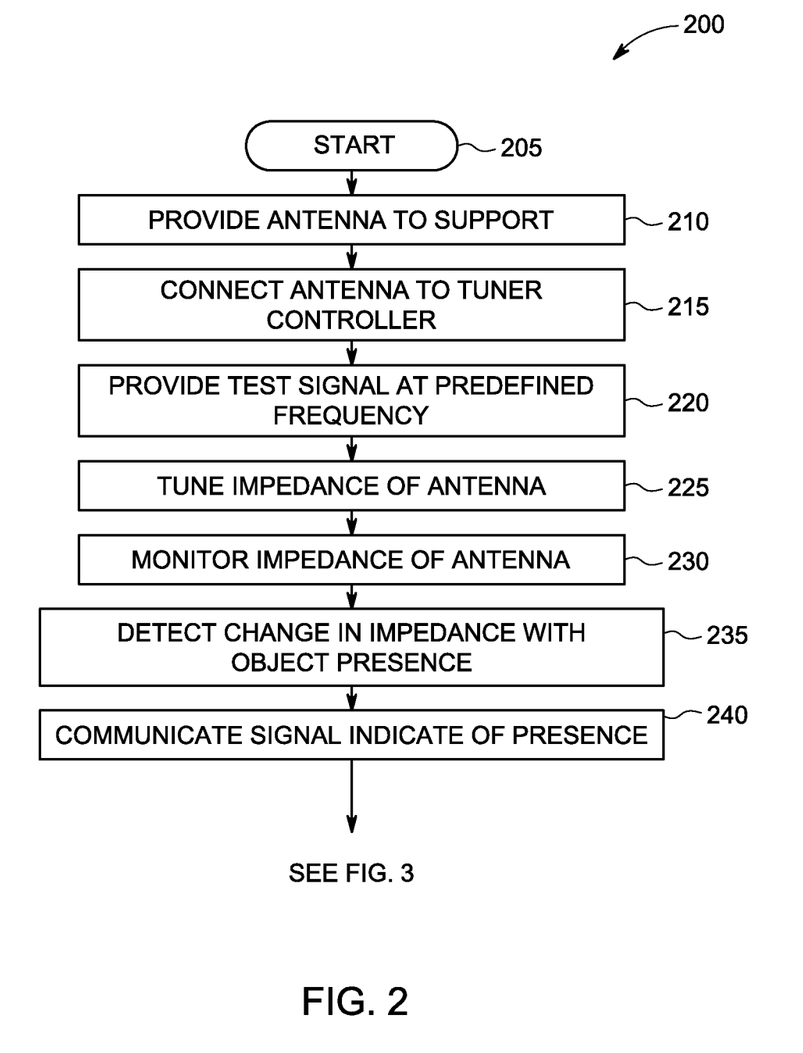
FIGS. 2 and 3 is a schematic flow diagram of an embodiment of a method of operating the system of FIG. 1 in accordance with subject matter described herein.

Step 205 can include the start of the method 200. Step 210 includes providing the antenna circuit 130 to the support 120. In one embodiment, the antenna circuit 130 is embedded within a structure of the support 120 (e.g., bed mattress) and in a configuration within a predefined distance of the outer circumference of the support 120. Step 215 includes connecting the antenna circuit 130 to the tag reader 125 in the proximity (e.g., same room or defined space) of the support 120 and the antenna circuit 130.

Step 220 can include the tag reader 125 providing a signal (e.g., alternating current) at a predefined frequency to the antenna circuit 130 with no object 110 present on the support 120. Step 225 can include tuning an impedance of the antenna circuit 130. An embodiment of tuning an impedance of the antenna circuit 130 can include changing an impedance of the antenna circuit 130 until detecting a predefined pass through or filter of the signal (e.g., resonant frequency). In one embodiment, the tag reader 125 can include the tuning module 150 having a capacitance adjuster operable to automatically change the impedance (e.g., capacitance in series or parallel with) of the antenna circuit 130. An embodiment of the antenna circuit 130 can also be a tuned antenna circuit 130 having the tuning circuit 155 in series or parallel with the antenna circuit 130. An embodiment of the tuning circuit 155 can be configured to have at least one slot to receive one or more capacitors in series or parallel with the antenna circuit 130 so as to adjust an impedance of the antenna circuit 130 in response to the signal from the tag reader 125. This can be an iterative process until the antenna circuit 130 is tuned at to the predefined frequency (e.g., resonant frequency) when the object 110 is not present on the bed support 120.

Step 230 can include monitoring change in impedance such as via the tag reader 125 providing test signal to the antenna circuit 130 and measuring for a predefined change in impedance of the antenna circuit 130 to test if a change in presence of the object 110 relative to the support 120. Step 230 can include the tag reader 125 sending the test signal and measuring for the change in impedance in response to detecting the tag 142 associated with the object 110 within a proximity of the tag reader 125. In the example where the object 110 is patient having an anatomical structure comprising a threshold composition of water that triggers the change impedance of the antenna circuit 130. However, application of the system 100 is limited to detecting presence of object 110 that is a person. The system 100 can be utilized in detecting the presence of various types of objects 110, dependent on an ability of the object 110 or its structural composition (e.g., water composition) to cause a threshold change in an impedance of the antenna circuit 130 receiving the object 110.

Further, although this description is directed where being "present" or the "presence" is of the object 110 (e.g. a person) on the support 120 (e.g., a bed), detection of the "presence" of the object 110 can vary from this example. For instance, detection of "presence" can be directed to the object 110 passing through a support 120 (e.g., the doorframe or window) or at a location or threshold proximity of the support 120 and is not limiting on the subject matter described herein.

Step 235 can include detecting change in impedance with change in presence of the object 110 relative to the support 120. Step 235 can include the tag reader 125 automatically adjusting the impedance of the antenna circuit 130 in response to detecting predefined deviation or change in impedance associated with the presence of the object 110 on the support 120 so as to re-tune the antenna circuit 130 to the predefined frequency (e.g., resonant frequency). In response to automatically adjusting or changing the impedance, step 240 can include the tag reader 125 communicating the presence signal indicative a change in present of the object 110 on the support 120. In this first example, the change in presence of the object 110 is associated with the object 110 first coming to rest on the support 120. The presence signal can be communicated to the controller 140 for transmission via the network 170 to the remote server 135.

Figure 3:
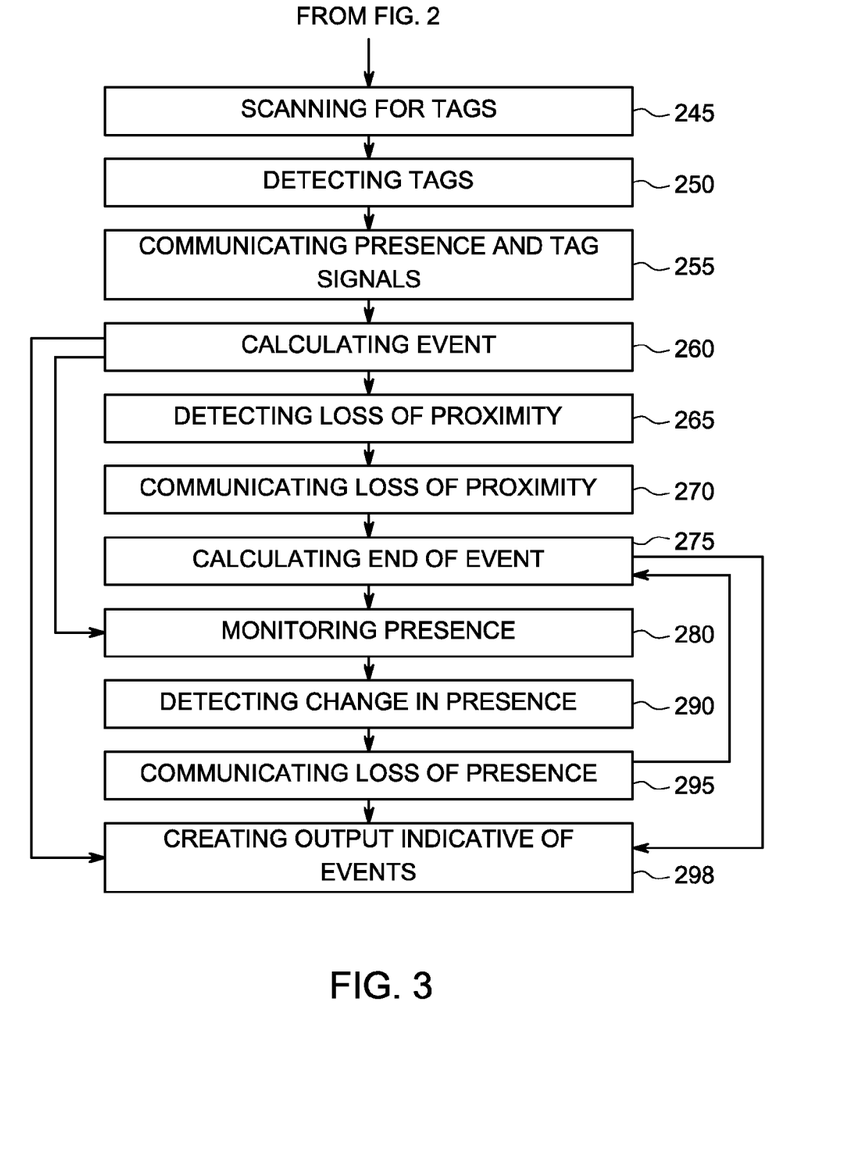

Step 245 can include the tag reader 125 scanning for tags 144, 146 associated with equipment 145 or caregiver personnel 147 in the room or defined space 149. Step 245 can be triggered in response to detecting the presence of the object 110 relative to the support 120. Step 250 can include the tag reader 125 detecting the tags associated with the equipment 145 or caregiver personnel 147 in the room or defined space 149. Step 250 can include the tag reader 125 communicating signal with tag information or data indicative of the unique identifier associated with the equipment 145 or caregiver personnel 147 to the controller 140. Step 255 can include the controller 140 communicating the presence signal and any tag signals associated with detected tags 144 or 146 to the remote server 135.

Step 260 can include the remote server 135 calculating an occurrence of one of a series of stored predetermined events dependent on receipt of the presence signal and the tag signal associated with the object 110, in combination with one or more tag signals associated with detection of the equipment 145 or caregiver personnel 147 in the proximity of the tag reader 125. The predetermined events can be stored in a database for retrieval by the remote server 135. The series of events can include predetermined tasks or protocol associated with the delivery of healthcare to the object 110 (ie, patient). Examples of events can include administering of medication by a caregiver 147, rounding by the caregiver 147, changing linens associated with the support 120, connection of a the object 110 (ie patient) to the equipment 145 (e.g., ventilator or ECG monitor), etc. known in operation of a healthcare facility in providing healthcare.

Step 265 can include detecting the tags 144 or 146 no longer within proximity of the tag reader 125. For example, the tag reader 125 can no longer detect a response associated with a periodic signal either sent to the tag or returned from the tag indicative of the tag (and associated object 110) leaving the proximity of the tag reader 125. In response, step 270 can include the controller 140 communicating a signal indicative of the loss and detecting the proximity of the tags 144, 146 to the remote server 135. Step 275 can include the remote server 135 calculating the end of any identified events associated with the equipment 145 or caregiver personnel 147 to the tags 144, 146, respectively.

Step 280 can include providing the test signal to the antenna circuit 130 and detecting the change in impedance of the antenna circuit 130. Step 280 can be executed in response to detecting the tag 142 no longer within a proximity of the tag reader 125, or in response to a periodic or generally continuous test signal provided by the tag reader 125 to the antenna circuit 130.

Step 290 can include detecting the change in impedance associated with the antenna circuit 130. In this example, the change in impedance would be associated with the object 110 leaving the presence on the support 120. Similar to the steps described above, the measure of the change in impedance can be associated with the tag reader 125 adjusting the impedance of the antenna circuit 130 until detecting the resonant frequency associated with the pass through of the test signal provided to the antenna circuit 130. Step 290 can be iterated until the tuner controller 125 detects return of the predefined resonant or baseline reference impedance (e.g., resonant frequency associated therewith) of the antenna circuit 130 with no presence of the object 110 relative to the support 120, as described in step 225.

Step 295 can include communicating a presence signal (or a non-presence signal different in frequency or amplitude or polarity) to the remote server 135 indicative of the loss of presence of the object 110 on the support 120. Step 298 can include creating an output 300 illustrative of the detection of event associated with the change in presence of the object 110 relative to the support 120 and proximity to tags 144, 146 associated with the equipment 145 or caregiver personnel 147 for viewing by the user of the system 100.

Figure 4:
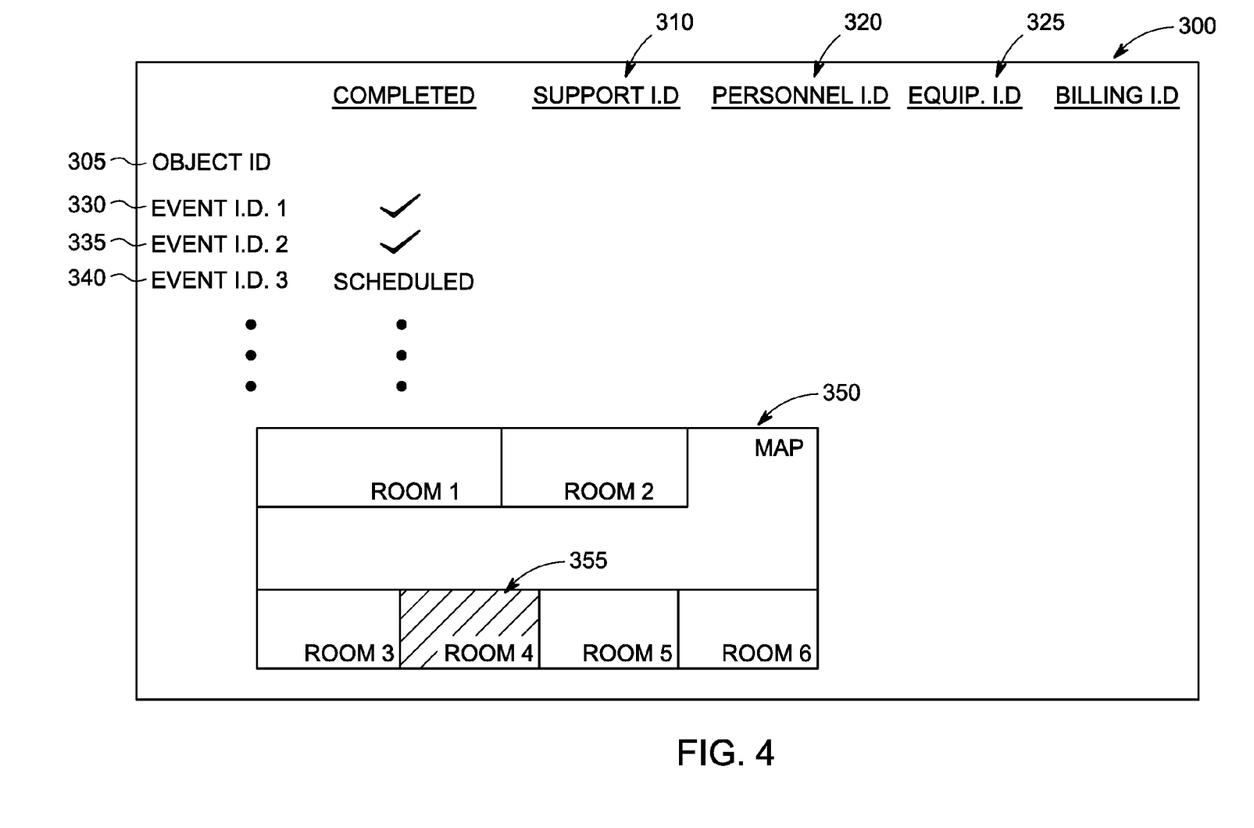
FIG. 4 is a schematic diagram of an embodiment of an illustration created by the system of FIG. 1 in accordance with subject matter described herein.

Referring now to FIG. 4, an example of the output 300 at the interface 175 can include a graphic illustration 305 of an identifier of the object 110, a graphic illustration 310 indicative of the change in presence or current status of the presence of the object 110 relative to the support 120 or defined space or room 149, a graphic illustration 320 indicative of the identifier of the caregiver personnel or graphic illustration 325 indicative of the equipment detected in proximity of the tag reader 125 during presence of the object 110 relative to the support 120. Based on detection of identifiers associated with the equipment 145 and caregiver personnel 147 in proximity of the tag reader 125 during presence of the object 110 (e.g., patient) relative to the support 120, the remote server can also create graphic illustrations 330, 335, 340 indicative of different events in delivery of tasks or protocol in healthcare. The types of graphic illustrations is not limiting on the subject matter described herein.

The output 300 can further include a graphic illustration 350 of a map of a unit or floor of a healthcare facility, including a graphic illustration 355 (shown in cross-hatch) indicative of the location of the presence of the object 110 relative to the support 120 for illustration to the operator or user of the system 100.

The system 100 described above is not limited to this one example of utilization in a healthcare facility, and can be utilized in various industrial settings or with respect to various objects 110 and is not limiting on the subject matter described herein. The support 120 utilizing the system 100 can vary, such as mobile supports (e.g., gurney, wheelchair, etc.), other types of static structural supports (e.g., chairs, etc.), and types of structural openings (door frame, window, etc.) and is not limiting on the subject matter described herein. Furthermore, the system 100 can be utilized in other environments, such as security in detecting unauthorized or authorized presence at locations or through entryways, or miscellaneous industrial settings where the system 100 can be utilized to detect presence of objects 110 that are inanimate or other living organisms (e.g., animals, plants, etc.) at locations or in proximity of supports.

A technical advantage of the subject matter described above is to provide a system 100 and method 200 to detect the event based on association of a presence of an object 110 at a location or support 120 relative to one or more other objects (e.g., caregiver personnel, equipment, etc.). In particular, this method can be used to detect different events associated with a protocol to deliver healthcare to a person located on or in proximity of a bed. The system 100 can be provide as a kit employing the antenna circuit with the support and using a low cost tag reader 125 and network 170 to communicate to the remote server 135. The system 100 can be used in a static environment such as a room, or portably relative to hallways or landmarks. The system 100 can provide low latency, high accuracy output 300 indicative of presence, proximity, etc. The system 100 can further include sensors 180 to supplement or confirm accuracy or enable further capability in calculating events as described above.

The system 100 also provides a low cost, flexible technology and method with a small footprint that can lower the barrier of entry into facilities and their infrastructure. With installation, the system 100 and method 200 can provide improved resolution of events occurring in general real-time in a complex, sometimes chaotic environment such as a hospital. The resolution can be into hospital operations such as utilization of equipment 145 or caregiver personnel 147, enable providing a better experience (e.g., less waiting) to the patients, as well as enable more efficient scheduling and execution of cleaning of equipment 145.

This written description uses examples to disclose the subject matter, and to enable one skilled in the art to make and use the invention. The patentable scope of the subject matter is defined by the following claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system to detect an event associated with a first object relative to a second object and a support, the system comprising:
an antenna provided on a support to receive the first object;
a tag reader in communication with the antenna and a tag located on the second object;
where in the tag reader can detect a change in a test signal generating a resonant frequency; and
a remote server in communication with the tag reader, wherein in response to detecting a change in impedance of the antenna associated with the presence of the first object, the tag reader communicates a presence signal to the remote server, and wherein in response to detecting the tag within a threshold proximity of the tag reader, the tag reader generates a tag signal for communication to a remote server, and wherein the remote server is operable to detect an association of the first and second objects based on a comparison of time associated with each of the tag signal and the presence signal and in response then create an output indicative of the association for illustration indicative of occurrence of the event.

2. The system of claim 1, wherein the first object is a person and the support is a bed.

3. The system of claim 1, wherein the second object is a mobile asset.

4. The system of claim 1, wherein the second object is a caregiver.

5. The system of claim 1, wherein the support is one of the group consisting of: a chair, a wheelchair, a gurney, a wall, and a door frame.

6. The system of claim 1, wherein the remote server detects an identification of one of multiple different events dependent on association of at least one tag associated with each object detected within proximity of tag reader within a threshold time period of detecting the presence of the first object relative to the support.

7. The system of claim 1, further including a second tag associated with the first object.

8. The system of claim 1, wherein the first object is a person having a patient tag, the support is a bed having a bed tag, and the second object is a caregiver having a caregiver tag, and wherein the remote server is operable to identify one from a plurality of different events in a delivery of healthcare to the person based on a comparison of a time of detecting the patient tag and the caregiver tag within a threshold proximity of the tag reader and a time of detecting the presence of the person relative to the bed.

9. The system of claim 1, wherein the tag reader detects an equipment tag associated with a unique identifier of an equipment within threshold proximity of the tag reader, and the remote server detects a second event associated with a unique identifier of the person relative to the bed based on the unique identifier of the caregiver associated with the caregiver tag and the unique identifier of the equipment associated with the equipment, and compares the event to determine a compliance to a predefined healthcare delivery step assigned to be provided to the person, the predefined healthcare delivery step stored at the system for retrieval by the remote server.

10. The system of claim 1, wherein in response to detecting the event, the remote server is operable to create an invoice to bill the person associated with a predefined charge for the event.

11. A method to detect an event associated with a first object relative to a second object and a support, the method comprising the steps of:

providing an antenna to receive the first object relative to the support;

detecting a change in impedance of the antenna associated with the presence of the first object via a tag reader;

where in the tag reader can detect a change in a test signal generating a resonant frequency;

communicating a presence signal to the remote server in response to detecting the change in impedance;

detecting the tag within a threshold proximity of the tag reader;

generating a tag signal for communication to a remote server in response to detecting the tag within threshold proximity of the tag reader;

detecting an association of the first and second objects at a remote server based on a comparison of time associated with each of the tag signal and the presence signal; and creating an output by the remote server indicative of the association for illustration indicative of the event.

12. The method of claim 11, wherein the remote server detects an identification of one of multiple different events dependent on association of at least one tag associated with each object detected within proximity of tag reader within a threshold time period of detecting the presence of the first object relative to the support.

13. The method of claim 11, wherein the first object is a person having a patient tag, the support is a bed having a bed tag, and the second object is a caregiver having a caregiver tag, and wherein the remote server identifies one from a plurality of different events in a delivery of healthcare to the person based on a comparison of a time of detecting the patient tag and the caregiver tag within a threshold proximity of the tag reader and a time of detecting the presence of the person relative to the bed.

14. The method of claim 11, wherein the tag reader detects an equipment tag associated with a unique identifier of an equipment within threshold proximity of the tag reader, and the remote server detects a second event associated with a unique identifier of the person relative to the bed based on the unique identifier of the caregiver associated with the caregiver tag and the unique identifier of the equipment associated with the equipment, and compares the event to determine a compliance to a predefined healthcare delivery step assigned to be provided to the person, the predefined healthcare delivery step stored at the system for retrieval by the remote server.

* * * * *